United States Patent [19]
McMurray

[11] Patent Number: 5,788,930
[45] Date of Patent: Aug. 4, 1998

[54] APPARATUS FOR PURIFYING AN ENVIRONMENT USING OZONE GENERATION

[76] Inventor: Larry Daniel McMurray, 14421 29th Ave. S., SeaTac, Wash. 98168

[21] Appl. No.: 701,120

[22] Filed: Aug. 21, 1996

[51] Int. Cl.$^6$ .............. A61L 9/015; B01J 19/08; B01J 7/00

[52] U.S. Cl. .............. 422/121; 422/186.12; 422/186.07; 422/186.14; 422/305; 422/105; 422/107; 422/120; 422/123

[58] Field of Search ..................... 422/102, 123, 422/186, 305, 120, 107, 121, 110, 186.12, 186.07, 186.14

[56] References Cited

U.S. PATENT DOCUMENTS

| | | | |
|---|---|---|---|
| 4,240,798 | 12/1980 | Wendelin et al. | 23/230 |
| 4,842,829 | 6/1989 | Hirai et al. | 422/186.08 |
| 4,853,735 | 8/1989 | Kodama et al. | 355/215 |
| 4,863,701 | 9/1989 | McMurray | 423/186.08 |
| 5,256,377 | 10/1993 | Nakamaru et al. | 422/122 |
| 5,368,816 | 11/1994 | Detzer | 422/28 |
| 5,514,345 | 5/1996 | Garbutt et al. | 422/124 |
| 5,573,730 | 11/1996 | Gillum | 422/123 |

FOREIGN PATENT DOCUMENTS 02297766  10/1992  Japan.

*Primary Examiner*—Stephen Walsh
*Assistant Examiner*—Claire M. Kaufman
*Attorney, Agent, or Firm*—Mark Zovko

[57] ABSTRACT

Apparatus for safely deodorizing and purifying an enclosure such as a building structure or vehicle using an ozone generator thereby minimizing the risk of biological exposure and pollutants which trigger environmental illness or allergic reactions. The ozone generator is controlled with an electronic logic circuitry and sensors which automatically regulates ozone exposures to peak at an antiseptic level thereby preventing inadvertent oxidation damage due to over exposure. One embodiment of the apparatus uses an ozone decomposing material to eliminate the harmful residual ozone concentration within the enclosure which is present immediately after an effective ozone treatment. Another embodiment allows for control of the apparatus from outside the enclosure being purified, allowing the operator to alter the outcome of the treatment.

7 Claims, 6 Drawing Sheets

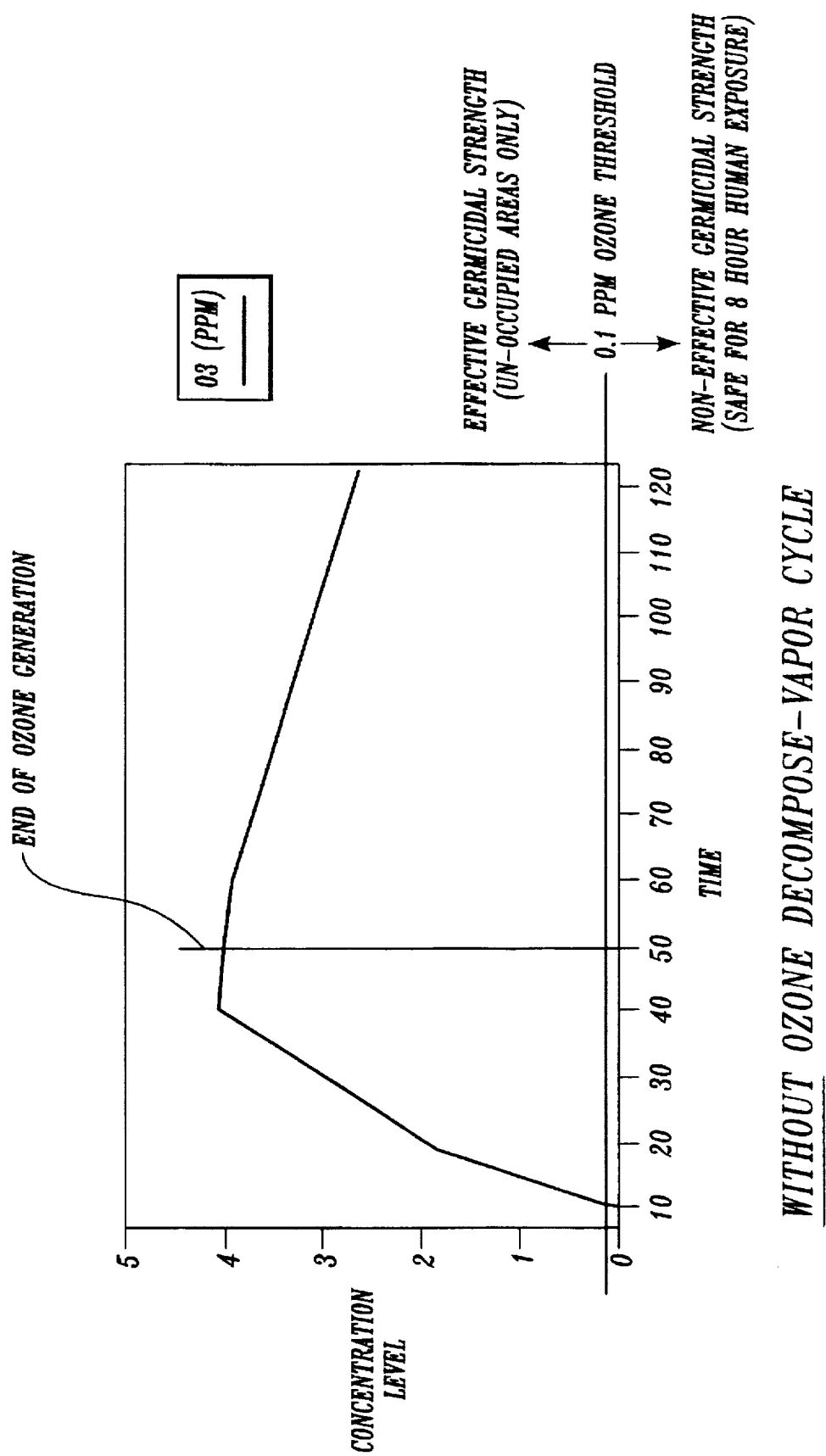

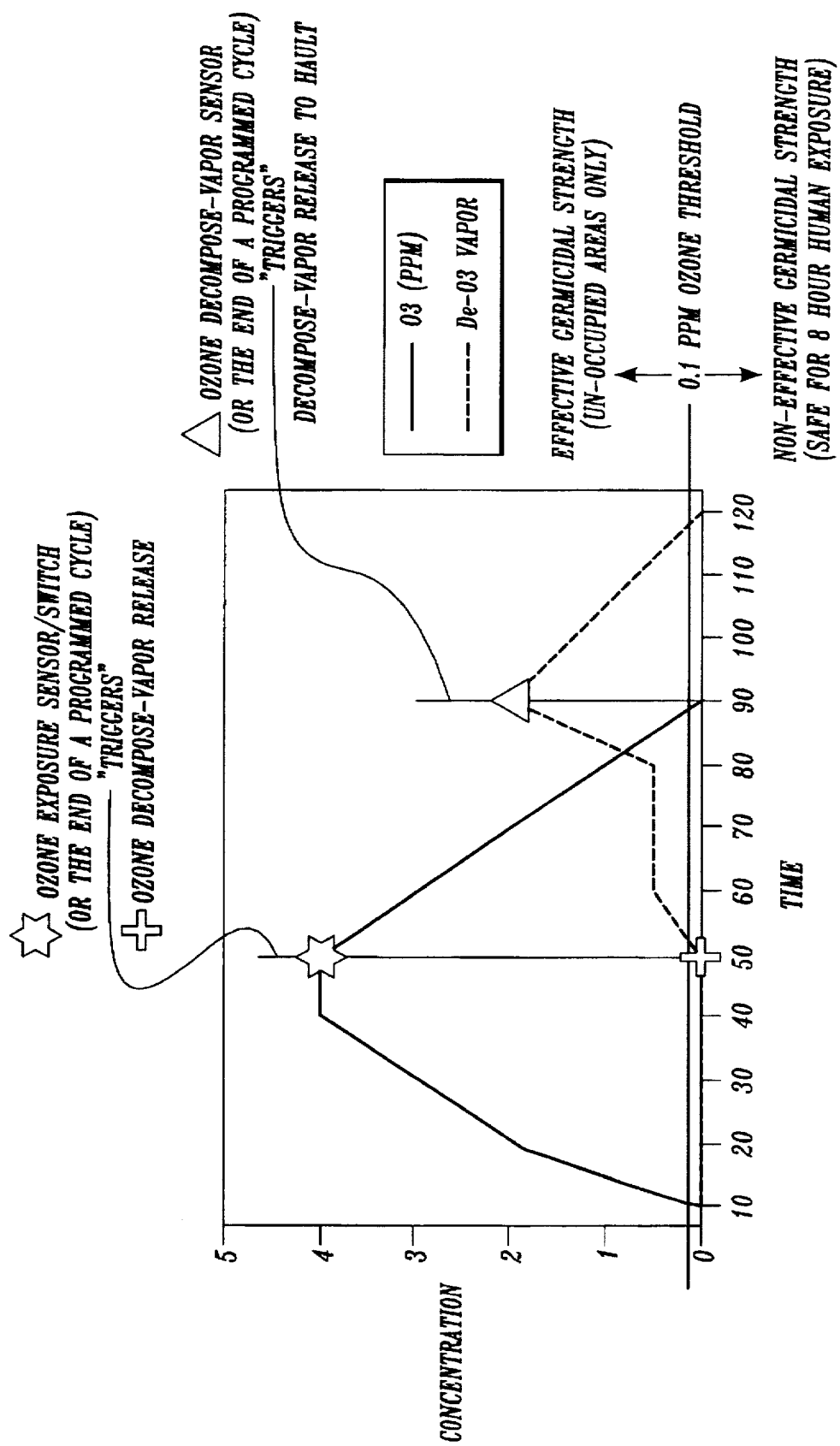

OPEN SWITCH

CLOSED SWITCH

APPARATUS FOR PURIFYING AN ENVIRONMENT USING OZONE GENERATION

BACKGROUND OF THE INVENTION

1. Field of the Invention

This application relates in general to apparatus for producing ozone for the elimination of chemical odor, germs, and other organic particulate matter in an enclosed space, and more particularly to ozone generating apparatus using sensors which allow the personal safety, efficient purification, and damage prevention associated with well known adverse effects of ozone overexposure in an enclosure.

2. Description of the Prior Art

Ozone generating apparatus has a long history in the prior art. The present application focuses on a portable ozone generating device such as that disclosed in U.S. Pat. No. 4,863,701 issued to the present inventor on Sep. 5, 1989. In that device, ozone was generated by electrostatic discharge using an array of glass tubes each containing a conductive rod serving as a core. Adjacent tubes were parallel to each other and the conductive rod of each tube is connected to the secondary terminal of a high voltage transformer. The tubes containing the conductive rods serve as an electrode when the voltage transformer is activated thereby creating an electrostatic field. Oxygen molecules in the electrostatic field are transformed to form ozone molecules. This prior art apparatus can be applied to deodorizing an enclosed space with the addition of a fan to feed oxygen past the tube array and distribute the ozone that is generated. After the ozone generation cycle stops, and to reduce excess ozone concentration in the enclosure, the apparatus had an odor emitting chamber which opened allowing a substance of choice to cause breakdown of ozone molecules present. In this apparatus the ozone decomposing substance, intended to be a pleasant scent such as any one of the a number of perfumed scents, was released at the end of the ozone generating cycle in the same amount regardless of the amount of ozone present. A major drawback would occur if the ozone concentration in the enclosure after deodorizing was high enough to break down the perfumed scent and remain at a high level. Monitoring of the ozone level in the enclosure or the level of perfiumed scent did not occur. Further, release of any ozone decomposing vapor was not controlled.

A search of the prior art has revealed several patents within the last decade which attempt to monitor the ozone generating cycle.

| U.S. Pat. No. | Inventor | Issue Date |
| --- | --- | --- |
| 5,368,816 | Detzer | 11/26/94 |
| 5,266,275 | Faddis | 11/30/93 |
| 5,256,377 | Nakamaru, et al | 10/26/93 |
| 4,842,829 | Hirai, et al | 6/27/89 |
| 4,853,735 | Kodama, et al | 8/1/89 |

Generally, these patents differ from the present invention which provides an air and surface antiseptic purifying system using ozone and electronic logic circuitry used to monitor operating cycles according to feedback from sensors. Apparatus used to purify enclosures has strict safety considerations as ozone in suitable germicidal concentration can be harmful to human or animal life. (See 21 CFR 801.415) It is imperative that ozone generating apparatus to be successfully employed have safeguards built-in to the apparatus which assure its fail-safe operation. Each of the above patent has a safe use of ozone generating apparatus as a goal but the individual embodiments differ from applicant. For example, in U. S. Pat. No. 5,368,816 issued to Detzer, ozone is added to a stream of air circulating through an air conditioning system to oxidize pollutants. A filter downstream of the ozone generating device is used to decompose any ozone after this operation. Sensors further downstream detect if the ozone concentration of the conditioned are as below a minimum safety level. Applicant's device, in contrast, does not require a filter, nor a sensor which detects ozone over a preset level resulting in a shut down of the entire system. The other patents in the search differ in structural and/or functional features relative to the present application and are cited of interest in a general nature. The teachings of these patents alone or in combination, would not anticipate or render obvious applicant's invention as later claimed in this application.

A major problem in ozone application in an enclosure continues to be possible damage due to ozone concentrations over a period of time. Ozone is known to cause premature aging of rubber items, plant foliage and other material affected by oxidation. A device set to run 12 hours in an enclosure may take only two hours to purify that environment with ozone, or may take twelve hours depending on the pollutants and odor present in the enclosure. It is desired to fmd an apparatus which will produce only enough ozone required to purify the environment without exposing the susceptible contents of the enclosure to ozone degradation. The present invention seeks to solve this problem.

SUMMARY OF THE INVENTION

The present invention has as its purpose the safe and efficient purification of an enclosures, such as a structured building or vehicle. An ozone generating device is provided for producing a source of ozone in the enclosure such as the apparatus generally described in U.S. Pat. No. 4,863,701 issued to the present inventor. An ozone decomposing material is also available which can be introduced into the enclosure if preset limits on the ozone exposure level in the enclosure are exceeded. To trigger the introduction of the ozone decomposing material a control system is used which includes an ozone sensor to monitor the ozone concentration in the enclosure and electronic logic circuitry to feedback the output from the ozone sensor to a controlling device which can initiate release of the ozone decomposing material into the enclosure. The ozone sensor may be remote to the ozone generator which is contemplated to be portable and within the enclosure. In one embodiment of the invention, the control system can include a contact switch which is held closed by spring action similar to automotive ignition points. A material which decomposes in the presence of ozone can be placed between the two contact surfaces of the switch thus holding the switch open by acting as an insulator until the material decomposes and fails in the ozone rich environment. A useful material for this purpose is latex such as that used in surgical gloves. The contact switch of this control system also can be used as a self limiting switch to terminate ozone treatment at a predetermined exposure thereby preventing unwanted damage due to excessive ozone exposure.

In an alternative embodiment of the invention, the apparatus can have an ozone generator and an ozone decomposing material available for release after the ozone generating cycle is complete. The control system of this embodiment includes a sensor for sensing a preset level of the ozone decomposing material as in theory, the molecules of the ozone decomposing material such as propane molecules will react with residual ozone until the ozone is consumed. At this point the sensor which can be designated a "combustion" sensor will sense a preset concentration of propane molecules present and stop the further release of propane molecules into the enclosure.

The sensor in this embodiment may be located outside of the ozone generating apparatus.

Two other embodiments of the invention are noteworthy. First, to safeguard the enclosure during purification, a motion sensor can be used which would detect any motion within the boundaries of the enclosure such as the inadvertent entrance of a person. The motion sensor would feedback to the ozone generating apparatus to stop the production of ozone until the apparatus is reset. The motion sensor could also, upon detection of motion within the enclosure, send a signal to introduce ozone decomposing vapor normally used after the ozone cycle is completed. Secondly, yet another embodiment contemplates remote control of the apparatus from a point outside of the enclosure. The ozone generating apparatus and ozone decomposing material capable of being released are located as before within the enclosure. The controls for controlling the ozone production cycle and the controls for releasing the ozone decomposing material are located outside of the enclosure. Sensing devices would signal readings to an operator outside of the enclosure. The operator can proceed with the purification of the enclosure and subsequent release of ozone decomposing material while maintaining a high degree of control over both of these functions. Also, it is possible for the ozone decomposing material module to be located separate from the ozone generator.

It is, therefore, an object of the present invention to provide a safe, effective apparatus for purifying an enclosure using electronic logic as part of a control system.

Another object of the present invention is to provide an apparatus which prevents high residual ozone levels in an enclosure after purification.

A further object of the present invention is to provide a portable ozone generating apparatus for purifying a closed environment.

Yet another object of the present invention is to provide safeguards to an ozone generating apparatus which responds directly to high residual ozone levels in an enclosure.

Another object of the present invention is to provide a ozone generating apparatus which uses a latex switch to determine when a critical ozone exposure has been reached, thereby preventing damage to the contents of the enclosure.

These and other objects and advantages will become more apparent from the subsequent detailed description especially when taken in conjunction with the drawings.

BRIEF DESCRIPTION OF THE DRAWINGS

FIG. 4 shows a graph of ozone concentration vs. time for the ozone generating cycle of the present invention.

FIG. 5 shows a graph of concentration vs. time for an ozone generating cycle and an ozone decomposing cycle of the present invention.

DETAILED DESCRIPTION OF THE PREFERRED EMBODIMENT

Figure 1:
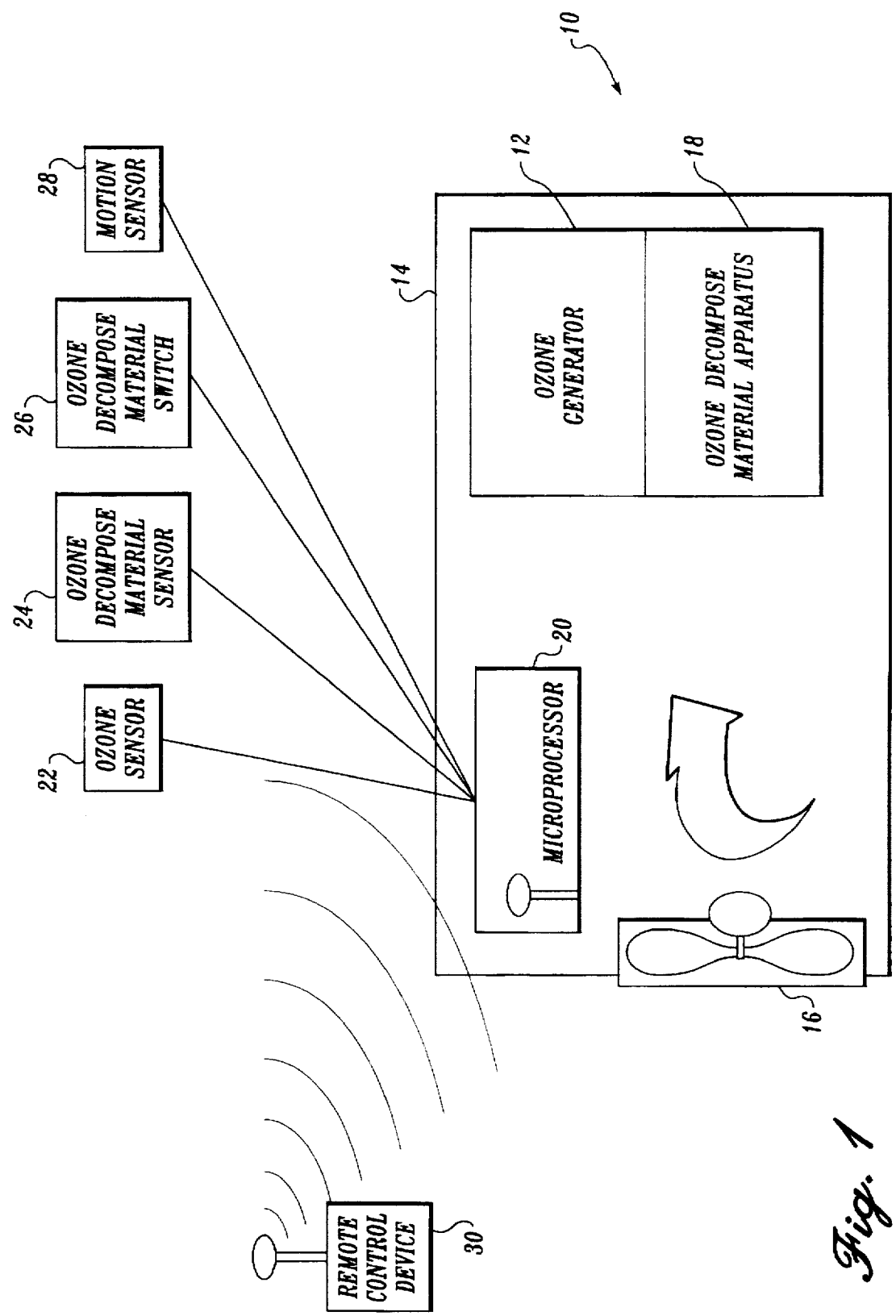
FIG. 1 is a schematic diagram of the apparatus of the present invention.

Referring to the Figures, the present invention can be described in detail. FIG. 1 shows schematically an apparatus for purifying an environment generally designated as 10. Purifying apparatus 10 has an ozone source or ozone generator 12 which can be similar to the apparatus disclosed in U.S. Pat. No. 4,863,701 issued to the present inventor. The ozone generator can be housed in housing 14 having a fan 16 to distribute ozone to the environment surrounding the apparatus 10. Also, enclosed in the housing 14 is an ozone decomposing material device 18 which is capable of emitting at the appropriate time to the environment surrounding apparatus 10, a material which decomposes ozone present in the environment over time. As part of the internal logic circuitry in the apparatus 10, a microprocessor 20 is provided within housing 14. The microprocessor can be connected to various sensors including an ozone sensor 22 and an ozone decomposing material sensor 24. Output from the ozone sensor 22 is fed to the microprocessor 20 and can be used to shape the ozone generation cycle. Similarly, the ozone decomposing material sensor 24 inputs to the microprocessor which in turn can control the release of ozone decomposing material to the environment to be purified. The microprocessor 20 can be a microprocessor well known in the art. Also, both the ozone sensor 22 and ozone decomposing material sensor 24 can be located integrally with the apparatus 10 or remote to the apparatus 10 using well known adaptations. The ozone decomposing material cycle may include a switch 26 which is open during the part of the purifying cycle that ozone decomposing material is not needed and closed during that portion of the cycle when ozone decomposing material is needed. In an optional embodiment, a motion sensor 28 can be provided which would sense any motion in the environment due to the inadvertent entry of a moving being into that environment. The motion sensor can be a standard well known variety with its output connected to the microprocessor 20. In this embodiment, the entry of a human into the environment would immediately stop ozone generation and initiate ozone decomposing material release if the entry occurred during the ozone generating cycle. As yet another option the entire apparatus 10 can be placed in an enclosed environment and controlled with a remote control device 30 from outside of the environment. Such a remote control device again, would be standard in the art and operate, for example, on a radio frequency. In this way, manual override to the apparatus 10 is provided in a safe, effective manner.

Figure 2:
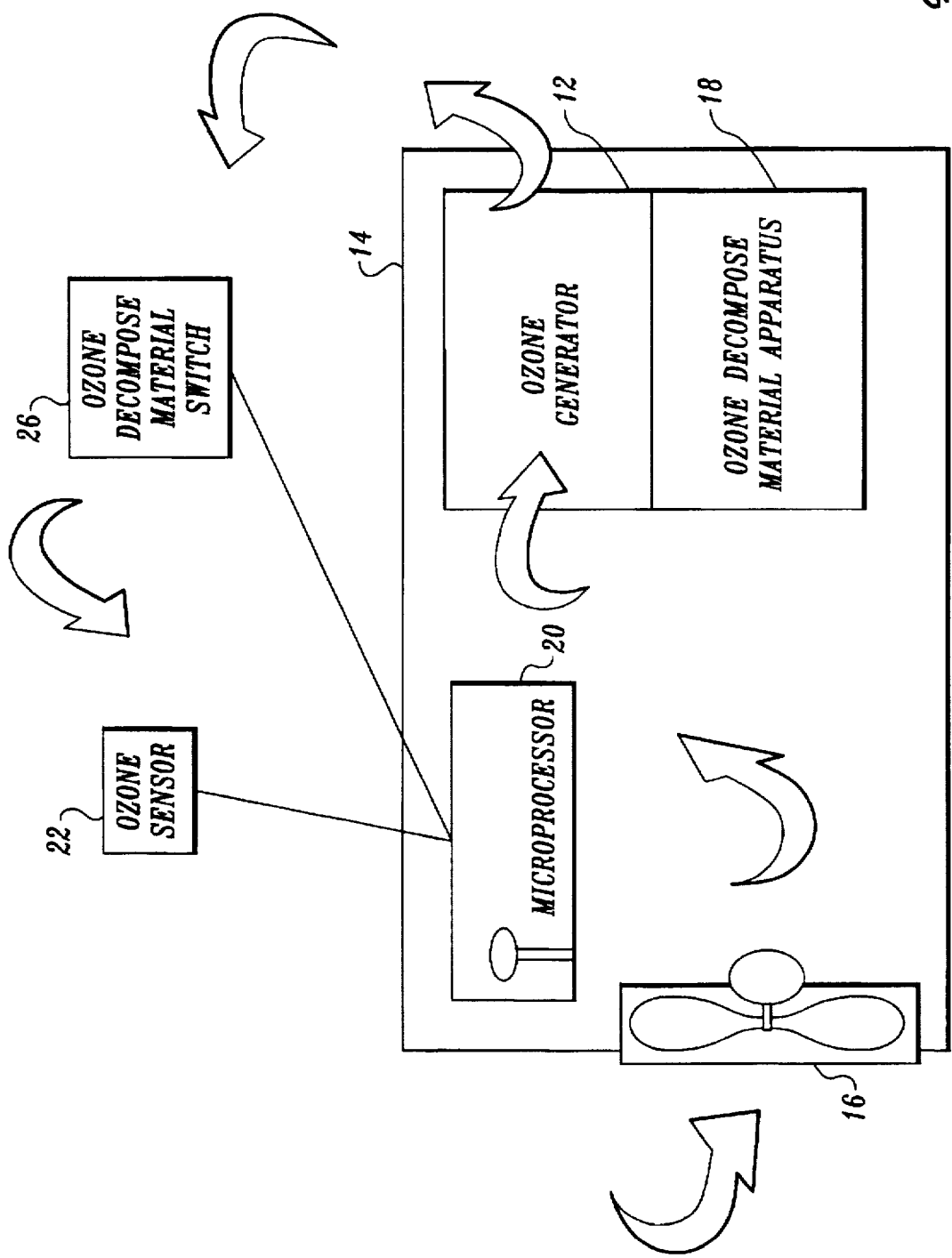
FIG. 2 is a schematic flow diagram showing the interplay between the generation of ozone and the ozone decomposing material switch.
Figure 3:
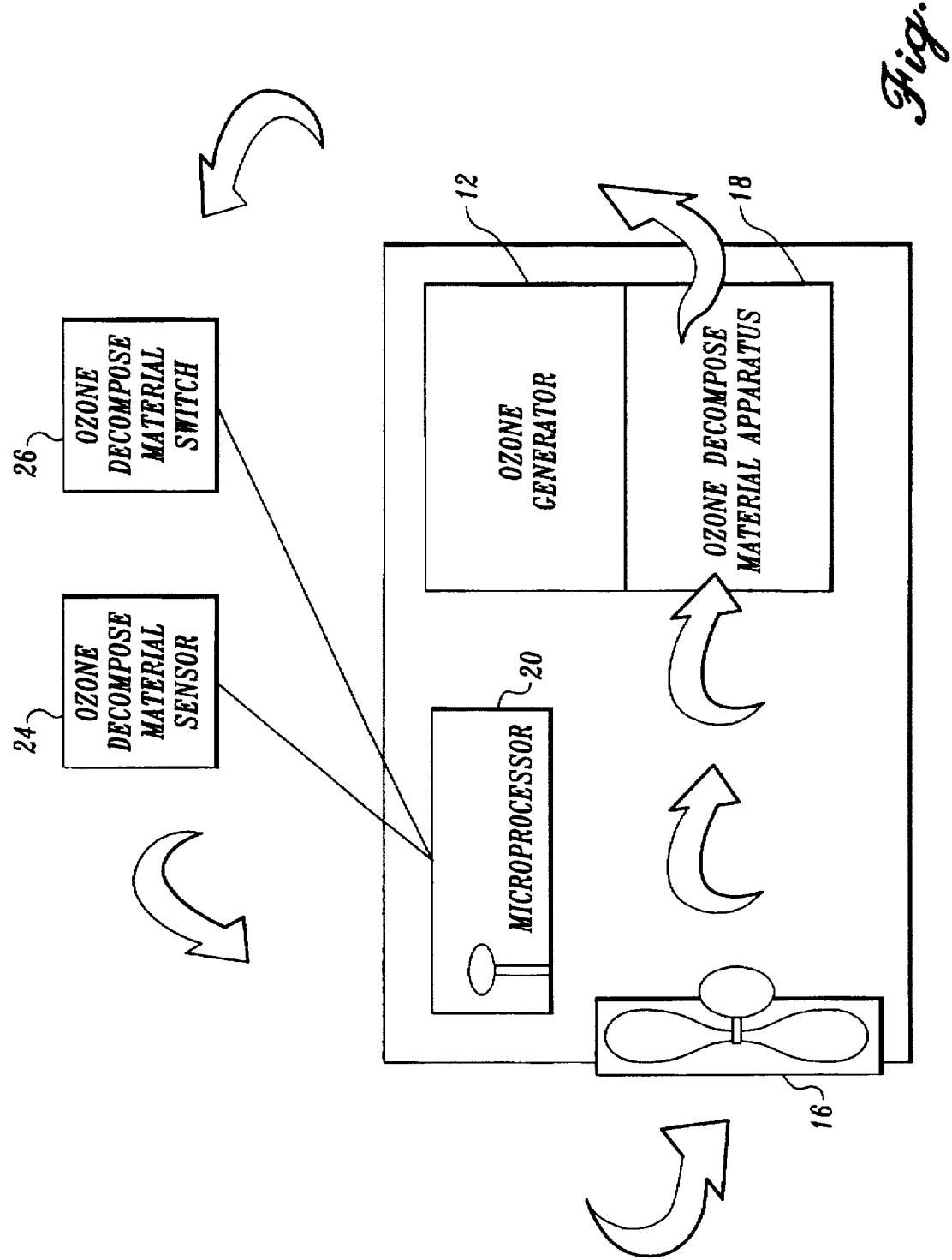
FIG. 3 is a schematic flow diagram showing the ozone decomposing material cycle.

Referring now to FIGS. 2 and 3, the flow of ozone generated in the apparatus 10 by ozone generator 12 to the surrounding environment during the ozone generating cycle is shown. FIG. 3 shows the ozone decomposing material cycle occurring after switch 26 has closed due to the appropriate signal from the ozone decomposing material sensor 24 or a preset ratio determined by the microprocessor 20 logic circuitry. These two cycles shown are controlled by the microprocessor 20 and/or by receiving signals from the sensors 22 and 24. FIG. 4 shows a graph of the ozone generating cycle using an ozone generator 12 alone without a ozone decomposing material release cycle. The graph shows ozone concentration in a typical environment to be purified over time. The peak antiseptic level ozone exposure occurs at shut-off (50 minutes) and gradually decreases to about 3 PPM at 120 minutes. If 0.1 PPM is a safe level for human exposure it is seen that the environment even after 2 hours ozone is still significantly present in the environment making human entry to that environment unsafe. Referring to FIG. 5, if the ozone decomposing cycle is added using an apparatus 10 described above, significantly different results occur. At 50 minutes, it is assumed that the ozone generating cycle is concluded either due to predetermined preprogramming or to the output from an ozone exposure sensor. At this point, the ozone decomposing material is released to the environment being purified and the concentration of that material increases over the next 40 minutes to a peak at 90 minutes. During this time, the ozone concentration in the environment has dropped below a 0.1 PPM threshold making the environment safe for 8 hour human exposure. At 90 minutes in the example shown, entry of the ozone decomposing material to the environment being purified is halted either by predetermined preprogramming or due to the output of a sensor (such as sensor 24 in FIG. 1) to the microprocessor of the apparatus. As shown in the graph of FIG. 5, the ozone decomposing material dissipates relatively rapidly over the next 30 minutes to a negligible concentration. The overall result is that the environment is purified by ozone, the ozone remaining from the ozone generating cycle is broken down by release of an ozone decomposing material, and the residual concentration of the ozone decomposing material falls to a negligible amount in a relatively short time.

Figure 6A:
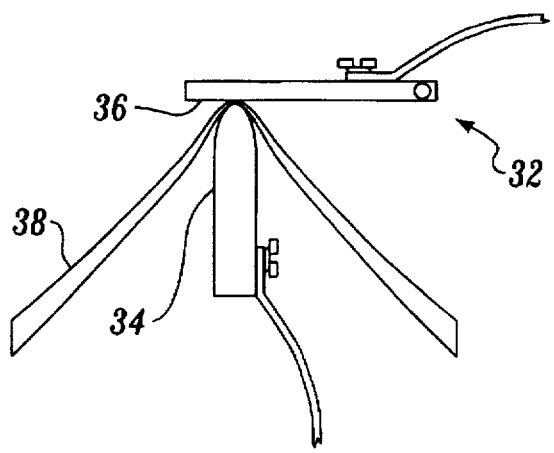
FIG. 6A shows a switch using a barrier for holding the switch open which is susceptible to ozone decomposition.
Figure 6B:
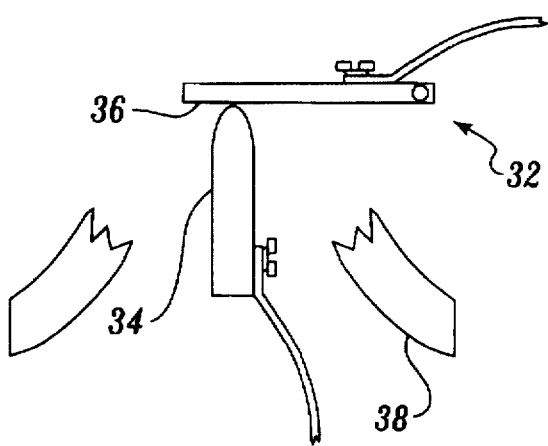
FIG. 6B shows the switch of FIG. 6A having the barrier broken thereby closing the switch.

Referring to FIGS. 6A and 6B an ozone decomposing material switch such as switch 26 of FIG. 1 is shown. This switch designated generally as 32, has a contact 34 and a contact 36 separated by a material 38 which is degradable by ozone, such as latex. In the normal mode the switch 32 is prevented from being closed by the presence of material 38. After degradation over time by ozone, the material 38 will fail, thereby allowing switch 32 to close due to contacts 34 and 36 touching. This switch 32 can be used to initiate the introduction of the ozone decomposing material into the environment to be purified by acting as an ozone exposure sensor.

The ozone decomposing material used in conjunction with the present invention can include a variety of organic materials. It is well known that any organic molecules will break down ozone, however, it is obvious that certain organic materials are more suitable than others in this application. One such recommended material is odorless propane which is available readily. This material works effectively to break down ozone molecules, does not impart undesirable odors, and is harmless to most environments and their contents.

The invention may be embodied in other forms without departing from the spirit or essential characteristics thereof. The present embodiments are therefore to be considered in all respects as illustrative and not restrictive, the scope of the invention being indicated by the appended claims rather than the foregoing description, and all changes which comes within the meaning and range of equivalency of claims are intended to be embraced therein.

What I claim is:

1. Apparatus for purifying an enclosure comprising
   a. ozone generating means for introducing ozone into the enclosure thereby purifying the enclosure;
   b. ozone decomposing means for introducing an ozone decomposing material into the enclosure at a predetermined ozone exposure duration within the enclosure; and
   c. control means for controlling the ozone concentration exposure within the enclosure and controlling the operation of said ozone decomposing means whereby the ozone concentration in the enclosure after purification can be regulated, said control means including sensor means for sensing the ozone concentration exposure and switch means having a decomposable material which decomposes in the presence of ozone, and said decomposable material contacting said switch means whereby said switch means will close when ozone decomposes said decomposable material thereby stopping the generation of ozone from said ozone generating apparatus.

2. The apparatus of claim 1 wherein said sensor means is located outside of said ozone generating apparatus.

3. The apparatus of claim 1 which includes motion sensor means for sensing motion within the enclosure, said motion sensor means stopping the generation of ozone from said ozone generating means if motion within the enclosure is detected.

4. The apparatus of claim 3 wherein said motion sensor means starts ozone decomposition if motion in the enclosure is detected.

5. The apparatus of claim 1 wherein said control means is located at least partially at a location outside of the enclosure.

6. Apparatus for purifying an enclosure comprising
   a. Ozone generating means for introducing ozone into the enclosure thereby purifying the enclosure;
   b. ozone decomposing means for introducing an ozone decomposing material into the enclosure after the apparatus purifies the enclosure; and
   c. control means for sensing determined concentration of said ozone decomposing material and controlling the amount of said ozone decomposing material released from said ozone decomposing means.

7. The apparatus of claim 6 wherein said control means includes sensor means located outside of said ozone generating means.

* * * * *